US00PP17523P3

(12) United States Plant Patent
Schlueter

(10) Patent No.: US PP17,523 P3
(45) Date of Patent: Mar. 27, 2007

(54) *HIBISCUS ROSA-SINENSIS* PLANT NAMED 'BIG BIRD'

(50) Latin Name: *Hibiscus rosa-sinensis*
Varietal Denomination: BIG BIRD

(75) Inventor: Barry Schlueter, Houston, TX (US)

(73) Assignee: Hines Nurseries, Inc., Irvine, CA (US)

( * ) Notice: Subject to any disclaimer, the term of this patent is extended or adjusted under 35 U.S.C. 154(b) by 26 days.

(21) Appl. No.: 11/207,515

(22) Filed: Aug. 19, 2005

(65) Prior Publication Data

US 2007/0044187 P1 Feb. 22, 2007

(51) Int. Cl.
*A01H 5/00* (2006.01)

(52) U.S. Cl. ..... Plt./257

(58) Field of Classification Search ..... Plt./257
See application file for complete search history.

*Primary Examiner*—Kent Bell
(74) *Attorney, Agent, or Firm*—Christie, Parker & Hale, LLP

(57) ABSTRACT

A new and distinct cultivar of *Hibiscus* plant named 'BIG BIRD', characterized by a large ruffled yellow flower with a dark maroon center. 'BIG BIRD' is a free flowering plant with an upright, compact habit, and glossy, dark green foliage.

4 Drawing Sheets

Botanical classification: *Hibiscus rosa-sinensis* L.
Varietal Denomination: The new plant has the varietal denomination 'BIG BIRD'.

BACKGROUND OF THE INVENTION

The present invention relates to a new and distinct cultivar of *Hibiscus,* botanically known as *Hibiscus rosa-sinensis* and hereinafter referred to by the cultivar name 'BIG BIRD'.

The genus *Hibiscus* comprises about 250 species of herbs, shrubs and trees in warm temperate and tropical regions; with leaves usually simple, mostly palmately veined, lobed or parted; flowers are mostly solitary in the leaf axils but sometimes in racemes, corymbs or panicles. *Hibiscus* is included in the family Malvaceae, which comprises about 95 genera of herbs, shrubs and trees originating in tropical and temperate regions. *Hibiscus rosa-sinensis* is a glabrate shrub, seldom over 8 feet tall in cultivation, but treelike to 15 feet or more in tropical regions. Leaves grow to 6-inches in length, and are ovate, usually serrate, mostly glossy green. Flowers are solitary in upper leaf axils.

The new *Hibiscus* is a product of a planned breeding program conducted by the Inventor in Webster, Tex. The objective of the program was to create new *Hibiscus* selections with improved bloom quality, color and floriferousness. A further objective was to produce plants that can be commercially produced on their own root systems, with improved plant habit, with regard to vigor and postproduction longevity.

The new variety was discovered in a controlled breeding program of *Hibiscus rosa-sinensis* and differs from its parents and other known cultivars of *Hibiscus rosa-sinensis* by the following characteristics in combination:

1. Upright, compact symmetrical plant habit that is suitable for container production;
2. Healthy dark green foliage;
3. Vigorous growth habit;

4. Large ruffled yellow flower with a dark maroon center; and
5. Free flowering.

SUMMARY OF THE INVENTION

The culitvar 'BIG BIRD' has not been observed under all possible environmental conditions. The phenotype may vary somewhat with variations in environment such as temperature, light intensity, nutrition and water status without, however, any variance in genotype.

The following traits have been repeatedly observed and are determined to be unique characteristics of 'BIG BIRD'. These characteristics in combination distinguish 'BIG BIRD' as a new and distinct cultivar:

1. Upright, compact symmetrical plant habit that is suitable for container production
2. Healthy dark green foliage.
3. Vigorous growth habit.
4. Large ruffled yellow flower with a dark maroon center.
5. Free flowering.

Asexual reproduction of the new variety by stem cuttings, performed in Webster, Tex. and Houston, Tex. have confirmed that the distinctive characteristics of the new variety are stable and transmitted to succeeding generations, and the new variety reproduces true to type.

COMPARISON WITH PARENTS AND OTHER CULTIVARS

'BIG BIRD' is distinguished from its female parent 'Spring Break' (not patented) by its flower color and size. Spring Break has an ivory bloom with a nearly black, star shaped eye. The flower on 'BIG BIRD' is consistently at least 2.5 cm greater in diameter than that on 'Spring Break'. 'BIG BIRD' is distinguished from its male parent, an unnamed, unpatented seedling of 'Stormy Moon' (not patented)×'Purple Passion' (not patented), in the flower color. The seedling selected from the cross of 'Stormy Moon'×'Purple Passion' has a grayed-purple flower while 'BIG BIRD' has a yellow flower with a dark maroon center.

The closest commercial cultivar to 'BIG BIRD' known by the Inventor is the unpatented cultivar 'Surf Rider'. However, in side-by-side comparisons conducted in Webster, Tex., plants of 'BIG BIRD' differ from plants of 'Surf Rider' in the following characteristics:

1. Flowers of the new *hibiscus* have a thicker texture than flowers on the cultivar 'Surf Rider';
2. Plants of the new *Hibiscus* are easier to clone via rooting than plants of the cultivar Surf Rider; and
3. Plants of the new *Hibiscus* possess a more upright growth than that of the cultivar 'Surf Rider', which is a low growing and prostate plant.

BRIEF DESCRIPTION OF THE DRAWINGS

The accompanying illustrations show a specimen of the new cultivar in a photographic illustration as true to color as is reasonably possible to make in an illustration of this character. Color values in the illustrations may differ slightly from the color values cited in the detailed botanical description, which accurately describes the actual colors of the new *Hibiscus*.

DETAILED DESCRIPTION OF THE INVENTION

Figure 1:
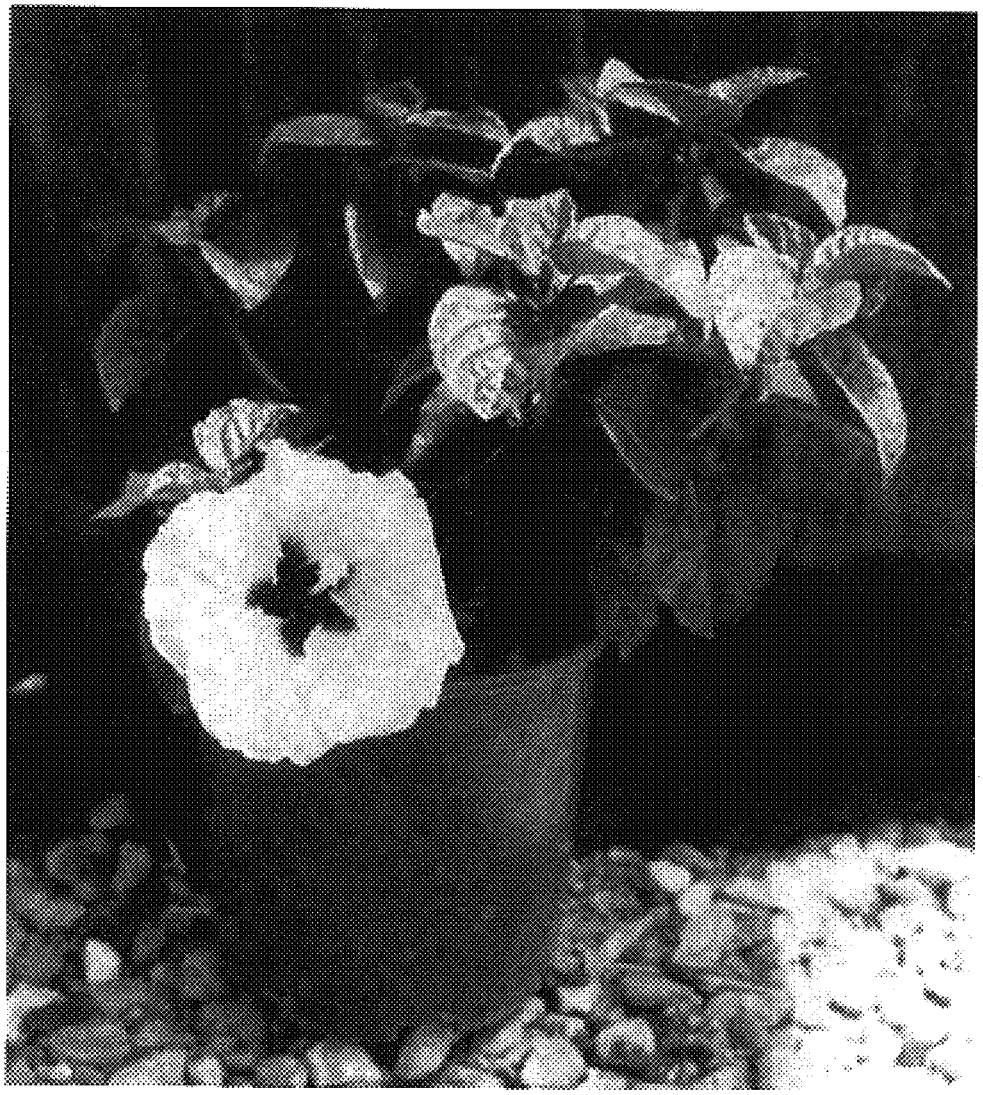
FIG. 1 illustrates a side perspective view of a typical plant of 'BIG BIRD'.
Figure 2:
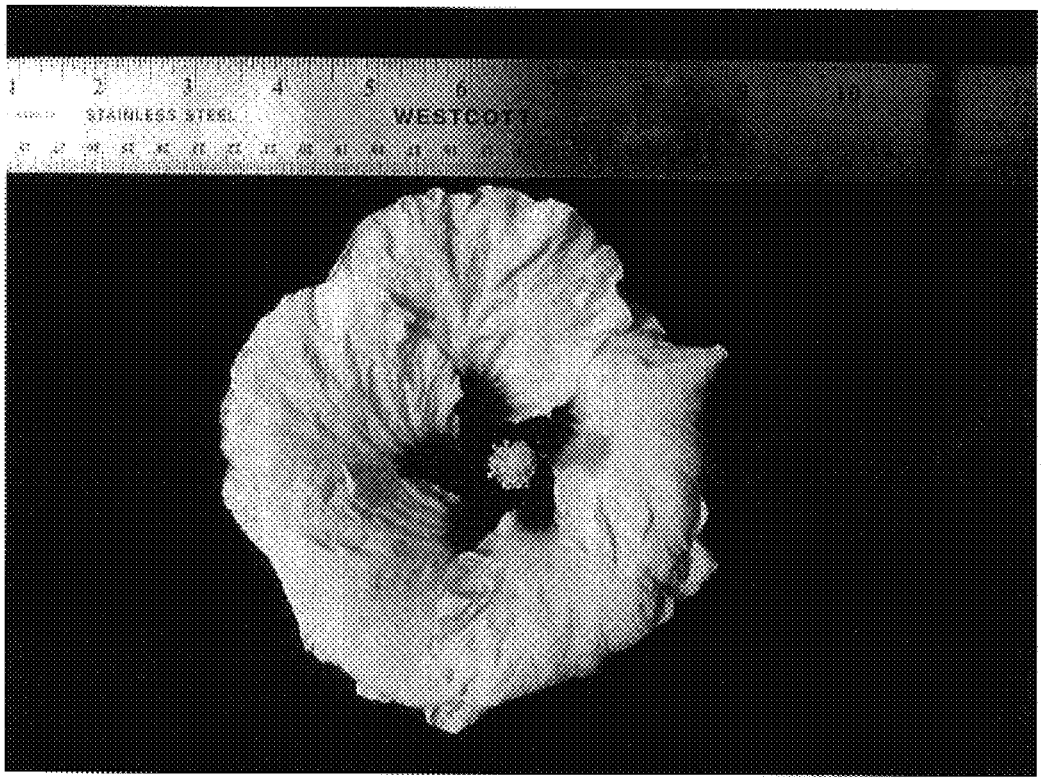
FIG. 2 illustrates the scale of a typical flower of 'BIG BIRD'.
Figure 3:
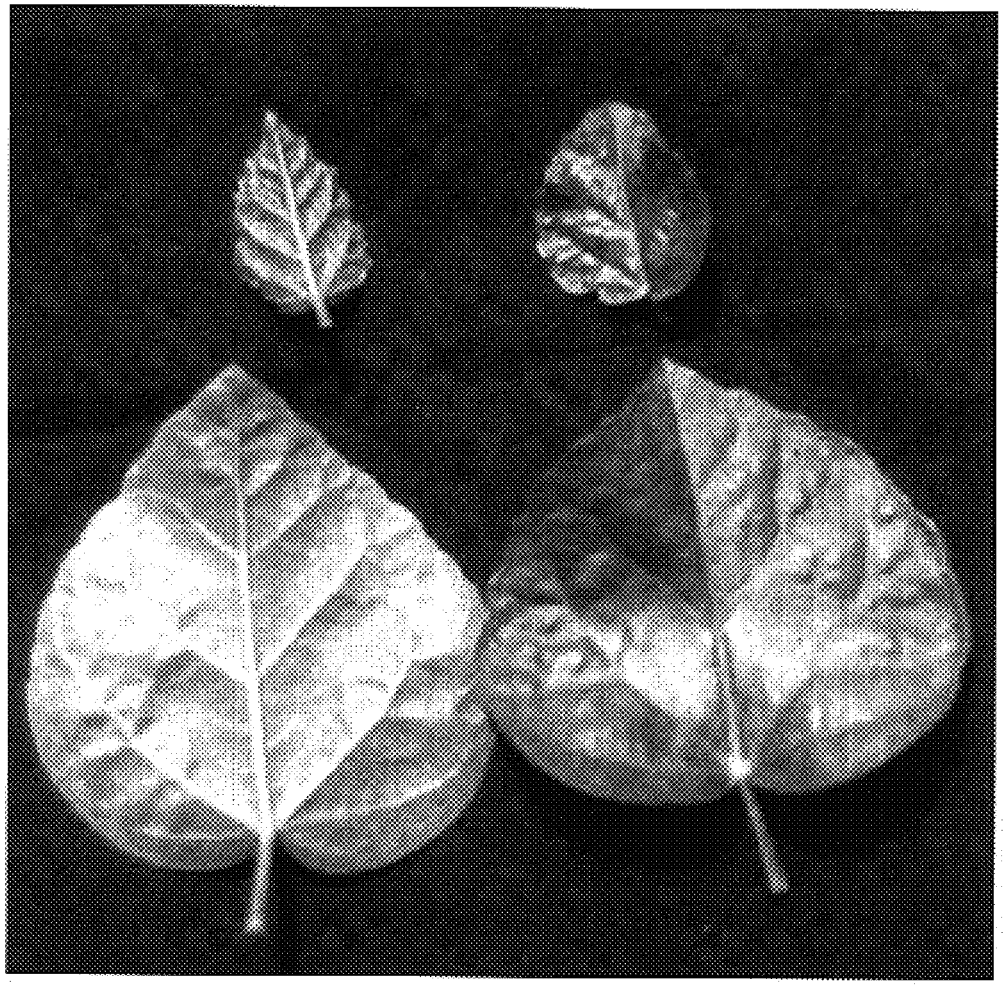
FIG. 3 illustrates the typical young to mature foliage of 'BIG BIRD'; the abaxial and adaxial surfaces are shown at each stage.
Figure 4:
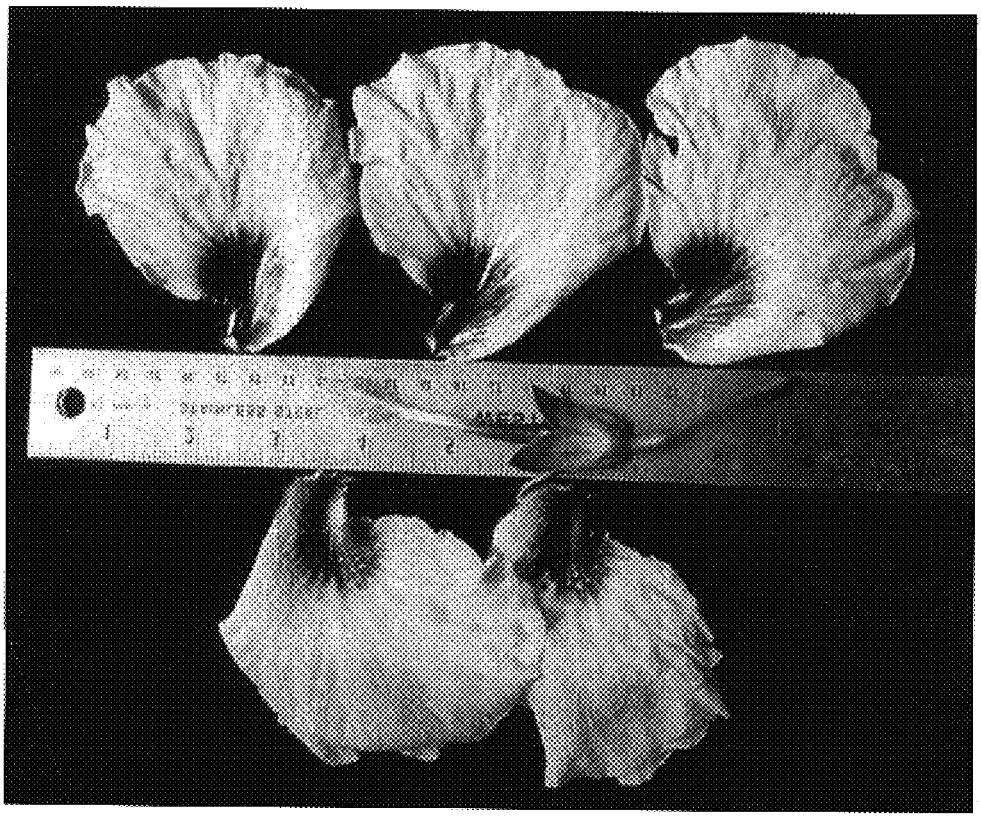
FIG. 4 illustrates a dissected flower of 'BIG BIRD', including shape and size of petals and characteristics of the reproductive structures.

'BIG BIRD' has not been observed under all possible environmental, cultural and light conditions. The following observations and descriptions are of plants grown in Fulshear, Tex., in April 2005, under polypropylene shade-cloth providing a 30 percent light reduction, and under conditions which closely approximate commercial production. Plants described were approximately one year old.

In this description, color references are to The Royal Horticultural Society Colour Chart (4th Edition) and terminology used in the color descriptions herein refers to plate numbers in this color chart. Phenotypic expression may vary with light intensity, cultural and environmental conditions.

Classification:

*Botanical.*—*Hibiscus rosa-sinensis* 'BIG BIRD'.

*Parentage.*—Female or Seed Parent: *Hibiscus rosa-sinensis* 'Spring Break'. Male or Pollen Parent: An unnamed plant from the cross of *Hibiscus rosa-sinensis* Stormy Moon×Purple Passion.

*Propagation.*—By cuttings.

*Time to initiate rooting.*—Approximately 14 to 21 days at 21–24° C.

*Time to develop roots.*—Approximately 42 to 56 days at 21–24° C.

*Root description.*—Fine to medium; fibrous; freely branching.

Plant:

*Size.*—Height: Approximately 40–50 cm in a #2 pot (from soil level to top of flowers). Diameter/Spread: Approximately 40–45 cm in a #2 pot.

*Form and growth habit.*—Perennial, evergreen shrub; mostly upright and somewhat spreading.

*Branching.*—Freely branching, about 4 to 8 lateral branches develop after pinching. Lateral Branches: Approximately 11 cm long and 4 mm in diameter. Coloration: Young — 147B. Mature — 199B. Internode Length: Approximately 3 cm.

Leaf:

*Shape.*—Cordate. Apex: Rounded. Base: Cordate.

*Leaf size.*—Approximately 9 cm long and 8 cm wide.

*Arrangement.*—Alternate, single, symmetrical.

*Margin.*—Crenate.

*Aspect.*—Undulate.

*Texture.*—Glabrous.

*Coloration.*—Young Foliage Upper side: Near Yellow-Green Group 146B. Under side: Near Yellow-Green Group 146C. Mature Foliage Upper side: Near Yellow-Green Group 147A. Under side: Near Yellow-Green Group 147B.

*Petioles.*—Size: Approximately 3 cm in length; approximately 2.5 mm in diameter. Coloration: Near Yellow-Green Group 147B. Texture: Smooth.

Inflorescence:

*Bloom period.*—Typically year-round under subtropical and tropical conditions.

*Flower arrangement.*—Arranged singly at terminal leaf axils; free flowering with 3 to 4 flower buds and/or open flowers per terminal apex; flowers face upright and slightly outward.

*Flower appearance.*—Ruffled yellow flower with a dark maroon center; flowers are open for about two days before closing; flowers persistent.

*Flower diameter.*—Approximately 14 cm.

*Flower depth.*—When placed on a horizontal plane, the flower extends 6 cm above the surface, with the ruffles extending 2 cm.

*Buds* (*just prior to showing color*).—Rate of Opening: Approximately 1 or 2 days, depending on temperature. Shape: Elliptic. Length: Approximately 3 cm. Diameter: Approximately 1.4 cm. Color: Near Yellow-Green Group 146B.

*Fragrance.*—None noted.

*Petals.*—Number/Arrangement: Corolla consists of 5 overlapping petals. Shape: Spatulate with rounded apex. Size: Approximately 8.5 cm long and 8.7 cm wide. Margin: Entire, but ruffled. Texture: Smooth. Base Descriptor: Oblique. Color Upper Surface: Yellow, near between 15A and 15B, with the eye or throat near greyed-purple 187A. Lower Surface: Majority of the lower surface is near 15C, fading to near 15D at the base of the petal.

*Sepals.*—Number/Arrangement: 5 sepals fused into a star-shaped calyx. Shape: Linear with acuminate apices. Margin: Entire. Color: Near Yellow-Green Group 146B.

*Peduncles.*—Length: Approximately 4 cm. Diameter: Approximately 2 mm. Angle: Upright to about 45 degrees. Strength: Strong, flexible. Color: Near Yellow-Green Group 147B.

Reproductive organs:

*Androecium.*—Stamens: Numerous; approximately 50. Stamen Length: Approximately 5 mm. Filament Color: Near White Group 155B. Anther Size: Approximately 1 mm long×1 mm wide. Pollen Amount: Abundant. Pollen Color: Near Yellow Group 15C.

*Gynoecium.*—Pistil Length: Approximately 6 cm. Stigma Appearance: Five, rounded. Stigma Diameter: Approximately 2 mm. Stigma Color: Near Yellow Group 5A. Style Color: Base is near 187A, lightening to near 185B; the upper half is near 15C. Seed Production: Has not been observed.

Pests/diseases: Resistance to known *Hibiscus* diseases had not been observed on plants grown under conditions approximating commercial practices.

What is claimed is:

1. A new *Hibiscus rosa-sinensis* plant named 'BIG BIRD', substantially as shown and described.

* * * * *